United States Patent [19]

Miwa et al.

[11] 4,444,891

[45] Apr. 24, 1984

[54] METHOD FOR TESTING TOXICITY OF CHEMICAL SUBSTANCE BY USING NEMATODE

[75] Inventors: Johji Miwa, Gifu; Mitsuru Furusawa, Nishinomiya, both of Japan

[73] Assignee: Duskin Franchise Co., Ltd., Osaka, Japan

[21] Appl. No.: 377,786

[22] Filed: May 13, 1982

Related U.S. Application Data

[63] Continuation of Ser. No. 149,722, May 14, 1980, abandoned.

[30] Foreign Application Priority Data

May 18, 1979 [JP] Japan .................................. 54-6053

[51] Int. Cl.³ ............................................ G01N 33/48
[52] U.S. Cl. .......................................... 436/2; 424/9; 435/29; 435/172; 436/183
[58] Field of Search ...................... 436/2, 183; 435/29, 435/849, 6, 172, 4; 424/9

[56] References Cited

U.S. PATENT DOCUMENTS 4,066,510  1/1978  Thilly ................................. 435/29 X
4,129,643  12/1978  Clayton ............................. 436/86 X

FOREIGN PATENT DOCUMENTS 658109  2/1963  Canada ................................. 435/29

OTHER PUBLICATIONS

Epstein et al., Chem. Abstr., vol. 82, 1975, No. 167804v.
Edgar et al., Science 198(4323) 1285–1286, Dec. 23, 1977.
Dusenbery, Chem. Abstr., vol. 81, No. 87533v.
Epstein et al., J. Mol. Biol. (1974) 90, 291–300.

*Primary Examiner*—Arnold Turk
*Attorney, Agent, or Firm*—Sherman & Shalloway

[57] ABSTRACT

Disclosed is a toxicity test for chemical substances using the phylum Nematoda.

According to this test, substances can be easily, rapidly, and inexpensively analyzed for their ability to induce mutations, promote tumor formation, act as teratogens, and cause abnormalities in development, metabolic function, and neuromuscular function.

11 Claims, No Drawings

METHOD FOR TESTING TOXICITY OF CHEMICAL SUBSTANCE BY USING NEMATODE

This application is a continuation of parent application Ser. No. 149,722, filed May 14, 1980, now abandoned.

BACKGROUND OF THE INVENTION

(1) Field of the Invention

The present invention is a method for testing the toxicity of a substance using the phylum Nematoda. Specifically, the invention is a test whereby substances can be easily, rapidly, and inexpensively analyzed for their ability to cause mutations, to promote tumors, to act as teratogens, and to affect embryogenesis, postembryogenesis, metabolic function, and neuromuscular function.

(2) Description of the Prior Art

Higher animals, such as mice, rats, rabbits, dogs, cats, pigs, and monkeys, are usually used as test animals in conducting toxicity tests of substances. When chronic toxicity tests are done, breeding must be carried out under carefully controlled conditions over a long period of 2 to 2½ years. Thus, performing such toxicity tests is very time consuming and expensive. Moreover, it is practically impossible to study genetic effects, such as mutagenicity of substances, because the length of time and high cost required are prohibitive.

In order to study mutagenicity of a substance, the bacterial mutation test using *Escherichia coli, salmonella,* or other bacteria, is often used. These bacteria, however, are prokaryotic organisms whose mechanism of gene expression is quite simple. They are quite different from multicellular organisms that possess higher levels of biological organization, such as embryogenesis. Accordingly, the bacterial mutation test is unsatifactory to detect substances that affect higher levels of biological organization.

In the chemical industry, novel chemical substances are continually being synthesized to meet various industrial and health requirements. Additionally, much research is being done to find new applications for known chemical substances. In each case, it is desirable to establish a rapid and inexpensive method for testing toxicity of these substances.

SUMMARY OF THE INVENTION

A primary object of this invention is to provide a rapid, easy, and inexpensive method for testing the toxicity of substances by analyzing their ability to cause mutation, to promote tumor formation, to act as teratogens, and cause abnormalities in development, metabolic function, and neuromuscular function.

Another object of this invention is to provide a method for testing toxicity of substances using an animal that is nonpathological, harmless, easily raised, and allows accurate and easy observation of test results.

Yet another object of this invention is to provide a method for testing mutagenicity of chemical substances easily and rapidly, using a nematode having a very short generation time.

In accordance with the present invention, these objects can be attained by a method for testing toxicity of substances, which comprises subjecting a nematode to the action of the substance to be tested.

DETAILED DESCRIPTION OF THE PREFERRED EMBODIMENTS

In the present invention, a nematode, such as Rhabditian, preferably a free-living self-fertilizing hermaphrodite, e.g. *Caenorhabditis elegans* or *Caenorhabditis briggsae,* is used as the test animal. This nematode is confirmed to be nonparasitic, nonpathogenic, and harmless. Furthermore, the cell division of this nematode from a fertilized egg to an adult and the process of organogenesis have been nearly completely traced and confirmed. Moreover, as the length of the adult animal is 1 mm, and egg, 0.06 mm, and as both the egg shell and body surface are transparent, the processes of embryogenesis and development of internal organs can be easily observed microscopically in the living animal.

This nematode can be easily cultured on agar medium in a petri plate, with *Escherichia coli* as a food source, or in liquid medium in a test tube or beaker. Even a person with little training can perform the toxicity test very easily if the test method using this nematode is adapted according to the present invention.

According to the test method of the present invention, expenses required for maintaining the test animal are small and the test procedures can be simply carried out in a small and confined space. Therefore, the total cost of the test can be remarkably low.

An additional advantage in the present invention is that the toxicity test can be completed in a very short period. The nematode, *Caenorhabditis elegans,* has a generation time of 2 to 4 days depending on temperature. Each hermaphrodite lays about 300 eggs, which grow to mature generative adults in about 50 hours. Thus, the mutagenicity and teratogenicity of a substance can be rapidly assayed.

As the nematode is a self-fertilizing hermaphrodite, crossing is unnecessary. Thus, mutations are naturally driven to homozygosity, and are, accordingly, easy to detect.

This is another great advantage of the present invention, using the above mentioned nematode.

Since the nematode that is used in the present invention is a metazoan animal, as are humans, influences of substances on higher animals can be predicted by analogy with test results obtained using this nematode. This is another prominant advantage of the present invention.

In the present invention, the nematode is subjected to the action of a substance to be tested. As an active control, another nemotode is exposed to a known toxic substance, e.g. ethyl methanesulfonate. In the case of a soluble chemical substance, this can be accomplished simply by adding the chemical substance to the nematode's culture medium. The amount of chemical substance to be added can optionally be changed, and influences of the concentration of the chemical substance can be easily examined.

The length of time for which the nematode is exposed to the action of a substance is not particularly limited. An appropriate length of time, most likely within one generation time, may be easily determined according to the kind and quantity of substance to be tested by a simple preliminary experiment.

After the nematode has been subjected to the action of the substance to be tested, it is transferred to a normal culture medium, for example, an agar medium with *Escherichia coli* as a food source, and allowed to propagate. Individuals of the resulting first filial generation ($F_1$) or second filial generation ($F_2$) are examined for presence of mutants, indicating the test substance is a mutagen.

Alternatively, the nematode is cultured in a medium containing a chemical substance to be tested (and, if necessary, transferred to normal media) and allowed to produce offspring.

By observing individuals or fertilized eggs of the nematode, the ability of the substance to promote tumor formation, to act as a teratogen, or cause abnormalities in development, metabolic function, or neuromuscular function can be determined.

The method of the present invention offers the advantage of being able to consistently trace the effect of the test substance throughout the events of ovulation, fertilization, and hatching, as well as embryonic and post-embryonic development with exactly predictable cell lineages and pattern formation. Effects of test substances on chromosomes can also be ascertained by the present invention.

Effects of the test substances can be tested in a short period by a relatively simple procedure. Accordingly, the test method of the present invention is remarkably advantageous economically over the conventional methods using other animals, and the test can be accomplished in a much shorter time than in the conventional test methods using other animals. Thus, it will be readily apparent that the present invention makes great economical, social, and hygienic contributions.

The nematode, Caenorhabditis elegans, is hermaphroditic and thus offers an advantage over Drosophila or other test animals because complicated crossing is not necessary and because mutants can be segregated in a high ratio. For example, if mutants of nematodes having a highly permeable cuticle are used as the test animal, the effects of very minute amounts of toxic substances can be detected. Moreover, screening of mutagenic substances can be further simplified by identifying reversion mutants, having normal movement, derived from uncoordinated or immobile mutants. Using mutants, such as having no repair enzymes, the sensitivity of the test method is further enhanced.

The present invention will now be described in detail with reference to the following examples, which by no means limit the scope of the invention.

EXAMPLE 1

A liquid culture medium having the following composition per liter was prepared and adjusted to pH 7.2.
$Na_2HPO_4$: 6.0 g
$KH_2PO_4$: 3.0 g
NaCl: 5.0 g
$MgSO_4$: 0.12 g
Glucose: 2.0 g
$H_2O$: 1 liter Wild-type Caenorhabditis elegans, normal in form and motion, were synchronized at the $L_1$ larval stage (among the 4 larval stages, $L_1$, $L_2$, $L_3$ and $L_4$) and inoculated to the above liquid medium.

In order to test the mutagenicity and teratogenicity of caffeine, five samples of the above culture were prepared. To each of these samples, various concentrations of caffeine or ethyl methanesulfonate, as an active control, were added.

5,000 ppm: Ethyl methanesulfonate (active control)
10,000 ppm: Caffeine
5,000 ppm: Caffeine
500 ppm: Caffeine
No chemical added (control)

Four hours after the addition of chemicals, each sample was washed of the chemicals. Sixty individuals (parents) from each sample were closed to petri dishes containing agar culture medium with Escherichia coli as a food source, allowed to mature at 24° C., and examined for developmental and behavioral abnormalities. The results are in Table 1.

TABLE 1

| Sample | Chemical Added | Developmental Abnormality (%) | Behavioral Abnormality (%) |
|---|---|---|---|
| A | 5,000 ppm of EMS* | 2.0 | 0.5 |
| B | 10,000 ppm of Caffeine | 37 | 11 |
| C | 5,000 ppm of Caffeine | 13 | 2.6 |
| D | 500 ppm of Caffeine | 0 | 0 |
| E | No chemical added (control) | 0 | 0 |

Note:
*EMS = Ethyl methanesulfonate

After about twenty $F_1$ eggs from each of the parents had been laid, the parents were removed, and the $F_1$ individuals were allowed to grow and reproduce many $F_2$ offsprings. The $F_2$ individuals were examined for presence of mutants having abnormal form, size, or movement. Table 2 shows the results.

TABLE 2

| Sample | Chemical Added | Abnormal form or size (%) | Abnormal Movement (%) |
|---|---|---|---|
| A | 5,000 ppm of EMS | 0.6 | 1.5 |
| B | 10,000 ppm of Caffeine | 0.1 | 0.2 |
| C | 5,000 ppm of Caffeine | 0.01 | 0.05 |
| D | 500 ppm of Caffeine | 0 | 0 |
| E | No chemical added (control) | 0 | 0 |

The results show that caffeine is both a mutagen and a teratogen.

EXAMPLE 2

The liquid culture medium containing about 1000 individuals of wild-type Caenorhabditis elegans per ml was prepared as in Example 1.

A synchronyzed Caenorhabditis elegans population was grown to adult on normal agar medium without added chemicals. The animals were transferred to the agar culture medium plate containing chemicals of various concentrations (Table 3) and grown for 1 day at 24° C. All worms were then washed from the agar medium plate leaving the eggs behind. The eggs were observed for 12 hours in order to trace the course of embryogenesis. The results are shown in Table 3.

TABLE 3

| Sample | Chemical Added | Abnormal Embryos (inclusive of dead embryos) (%) |
|---|---|---|
| F | 5,000 ppm of EMS | 30 |
| G | 250 ppm of PCDF* | 25 |
| H | 50 ppm of PCDF | 11 |
| I | 5 ppm of PCDF | 3 |
| J | No chemical added (control) | 1 |

Note:
*PCDF = 2,3,6,7-tetrachlorodibenzofuran

The results demonstrate that 2,3,6,7-tetrachlorodibenzofuran is a teratogen.

EXAMPLE 3

An agar culture medium having the following composition per liter was prepared and adjusted to pH 6.0 with 25 mM potassium phosphate buffer.
Agar: 15 g
Peptone: 3 g
NaCl: 3 g
Cholesterol: 5 mg
$MgSO_4$: 120 mg
$CaCl_2$: 55 mg
$H_2O$: 1 liter As test substances, 12-0-tetradecanoyl-phorbol-13-acetate (TPA), phorbol-12,13-didecanoate (PDD), phorbol, and 4-α-PDD were selected. Dimethylsulfoxide (DMSO) solutions of these test substances were added independently to the above medium. The final DMSO concentration was 0.1%. The concentrations of the test substances were as shown in Table 4.

Each agar culture plate containing a test substance was innoculated with Escherichia coli as a food source and incubated at 24° C. for 1 day. Then, 5 animals were added to each plate, allowed to grow and reproduce for 4 to 5 days, and examined for effects of the test substances. The results are shown in Table 4.

$L_1$ and $L_3$ larvae and young adults without eggs were used as the test animals.

TABLE 4

Effects of phorbol ester on Caenorhabditis elegans

| Test subst. | Dose g/ml | $L_1$ Brood size[1] | $L_1$ Comments | $L_3$ Brood size | $L_3$ Comments | Adult Brood size | Adult Comments |
|---|---|---|---|---|---|---|---|
| TPA | $10^{-6}$ | 0 | arr $L_{2-3}$,[2] unc[3] | 0 | arr $L_4$, unc | 128 | sal,[4] unc |
|  | $10^{-7}$ | 13 | unc | 76 | sal, unc | 118 | unc |
|  | $10^{-8}$ | 151 | nml[5] | >200 | nml | >200 | nml |
|  | $10^{-9}$ | >200 | nml | >200 | nml | >200 | nml |
| PDD | $10^{-6}$ | 0 | arr $L_{2-3}$, unc | 14 | sal, unc | 144 | sal, unc |
|  | $10^{-7}$ | 0 | arr $L_{3'}$, unc | 97 | sal, unc | 183 | unc |
|  | $10^{-8}$ | >200 | nml | >200 | nml | >200 | nml |
|  | $10^{-9}$ | >200 | nml | >200 | nml | >200 | nml |
| Phorbol | $10^{-6}$ | >200 | nml | >200 | nml | >200 | nml |
| 4-PDD | $10^{-6}$ | >200 | nml | >200 | nml | >200 | nml |
| DMSO | 0.1% | >200 | nml | >200 | nml | >200 | nml |
| None | — | >200 | nml | >200 | nml | >200 | nml |

Note:
[1] Number of progeny per parent.
[2] arr $L_{2-3}$: development arrested at $L_2$ or $L_3$ stage.
[3] unc: uncoordinated movement.
[4] sal: short adult life.
[5] nml: normal.

So far as we know, a method for simply, rapidly, and unambiguously screening a certain substance whether or not it has a promoter function in chemical carcinogenesis has not been established. From the results shown in Table 4, it is apparent that according to the toxicity testing method of the present invention, abnormal influences on nematodes can be simply and clearly confirmed with respect to TPA and PDD, which are known to have a promoter action in chemical carcinogenesis. Therefore, it will be readily understood that a method for simply, rapidly, and clearly screening promoters, which are significant factors in chemical carcinogenesis, is provided according to the present invention.

What we claim is:

1. A toxicity test method for chemical substances using a phylum nematoda, which comprises
    adding an active control and a chemical substance to be tested, said chemical being other than the active control, to separate culture media each containing a phylum nematoda which is a free-living, self-fertilizing hermaphrodite;
    exposing the nematoda to the action of the substance within one generation time;
    transferring the nematoda to a normal culture medium with Escherichia coli as a food source; allowing the nematoda to propagate; and examining individuals of the resulting first filial generation ($F_1$) or second filial generation ($F_2$) for the presence of mutants.

2. A toxicity test method according to claim 1 wherein the nematoda is Caenorabditis elegans or Caenorhabditis briggsae.

3. A toxicity test method for chemical substances using a phylum nematoda which comprises
    adding an active control and a chemical substance to be tested, said chemical being other than the active control, to separate culture media each containing a phylum nematoda which is a free-living, self-fertilizing hermaphrodite and which is synchronized at $L_1$ larvae stage;
    exposing the nematoda to the action of the substance within one generation time; transferring the nematoda to a normal culture medium with Escherichia coli as a food source; allowing the nematoda to mature; and
    examining individuals of adults for developmental and behavioral abnormalities.

4. A toxicity test method for chemical substances using a phylum nematoda which comprises
    allowing a synchronized Caenorhabditis elegans population to grow to adults on a normal agar culture;
    transferring said adults to separate agar culture media, one of said media containing an active control, the other medium containing a chemical substance to be tested, said chemical being other than the active control; allowing said adults to grow within one generation; removing the adults from each of the agar culture medium leaving the resulting eggs behind; and observing the eggs in order to trace the course of embryogenesis.

5. A toxicity test method for chemical substances using a phylum nematoda, which comprises
    adding a solution of an active control to a first agar culture medium; adding a solution of a chemical substance to be tested to a second agar culture medium, said chemical being other than the active control; inoculating both agar culture media with *Escherichia coli* as a food source to effect incubation;

adding test animals which are larvae or young adults of *Caenorhabditis elegans* without eggs to the agar culture media;

allowing the test animals to grow and reproduce for 4 and 5 days; and examining individuals of the test animals for effects of the active control and the chemical substance.

6. A toxicity test method for chemical substances using a phylum Nematoda, which comprises culturing a phylum Nematoda that is a self-fertilizing hermaphrodite in a culture medium; treating the nematode with the chemical substance to be tested; allowing the treated nematode ($F_0$) to propagate; and examining at least one of the treated parental nematode ($F_0$), offspring in the first-filial generation ($F_1$) and offspring in the second-filial generation ($F_2$).

7. A toxicity test method according to claim 6 wherein the nematode is free-living.

8. A toxicity method according to claim 6 wherein the nematode is *Caenorhabditis elegans* or *Caenorhabditis briggsae*.

9. A toxicity test method for chemical substances using a phylum Nematoda, which comprises culturing a phylum Nematoda that is a self-fertilizing hermaphrodite in a culture medium; treating the nematode at the embryonic, larval, or adult stage with the chemical substance to be tested; allowing the treated nematode ($F_0$) to propagate; and examining the treated parental nematode ($F_0$), offspring in the first-filial generation ($F_1$) and offspring in the second-filial generation ($F_2$) for at least one of developmental, behavioral, and reproductive abnormalities.

10. A toxicity test method according to claim 9 wherein the nematode to be treated is synchronized.

11. A toxicity test method according to claim 9 wherein the nematode to be treated is a young adult without eggs.

* * * * *